United States Patent
Wang et al.

(10) Patent No.: US 11,022,448 B2
(45) Date of Patent: Jun. 1, 2021

(54) COGNITIVE CONTEXTUAL ROUTE NAVIGATION

(71) Applicant: International Business Machines Corporation, Armonk, NY (US)

(72) Inventors: Bing Xin Wang, Beijing (CN); Zhuo JP Cai, Beijing (CN); Kushal Patel, Pune (IN); Sarvesh Patel, Pune (IN)

(73) Assignee: International Business Machines Corporation, Armonk, NY (US)

( * ) Notice: Subject to any disclaimer, the term of this patent is extended or adjusted under 35 U.S.C. 154(b) by 328 days.

(21) Appl. No.: 16/238,937

(22) Filed: Jan. 3, 2019

(65) Prior Publication Data

US 2020/0217677 A1 Jul. 9, 2020

(51) Int. Cl.
| | |
|---|---|
| *G01C 21/34* | (2006.01) |
| *G06N 20/00* | (2019.01) |
| *G06N 7/00* | (2006.01) |
| *G08G 1/123* | (2006.01) |
| *H04W 4/024* | (2018.01) |
| *A61B 5/00* | (2006.01) |

(52) U.S. Cl.
CPC ..... *G01C 21/3461* (2013.01); *G01C 21/3415* (2013.01); *G06N 7/005* (2013.01); *G06N 20/00* (2019.01); *A61B 5/7275* (2013.01); *H04W 4/024* (2018.02)

(58) Field of Classification Search
CPC ............ G01C 21/3461; G01C 21/3415; G06N 20/00; G06N 7/005; A61B 5/7275
USPC .......................................... 701/411, 527, 533
See application file for complete search history.

(56) References Cited

U.S. PATENT DOCUMENTS

| | | | |
|---|---|---|---|
| 8,744,766 B2 | 6/2014 | Rakshit | |
| 9,449,514 B2 | 9/2016 | Schunder et al. | |
| 9,683,860 B1 | 6/2017 | Kahn et al. | |
| 10,768,621 B1* | 9/2020 | Nix | G05D 1/0088 |
| 2013/0080053 A1* | 3/2013 | Rakshit | G01C 21/3461 |
| | | | 701/527 |

(Continued)

OTHER PUBLICATIONS

IP.com Search—1.*

(Continued)

*Primary Examiner* — Mahmoud S Ismail
(74) *Attorney, Agent, or Firm* — Heslin Rothenberg Farley & Mesiti P.C.; Scott Dobson, Esq.

(57) ABSTRACT

A method, computer program product, and a system include a processor(s) monitors activities of a user utilizing a navigational application to provide route guidance to a geographic destination. With permission of the user, the processor(s) monitors authorized data sources to obtain data relevant to the user and generate and train a predictive model to determine a probability that the user will experience a wellness issue based on experiencing environmental factors. The processor(s) obtains a request to receive route guidance to the desired destination, via the navigational application and generates a recommended route to the desired destination, based on applying the predictive model to environmental data obtained from a portion of the authorized data sources. The recommended route avoids one or more locations en route to the desired destination where there is a given environmental issue that the predictive model indicates will present a wellness issue for the user.

20 Claims, 9 Drawing Sheets

(56) References Cited

U.S. PATENT DOCUMENTS

2015/0142313 A1* 5/2015 Haberman ......... G01C 21/3415
                                                                  701/533
2017/0351832 A1* 12/2017 Cahan .................... G16H 70/60

OTHER PUBLICATIONS

IP.com Search—2.*
Mell et al., "The NIST Definition of Cloud Computing", National Institute of Standards and Technology, U.S. Dept. of Commerce, NIST Special Publ. 800-145, Sep. 2011, 7 pages.
Cognitive Personalized Risk Estimation System for Real-time Travel Route Recommendation, Disclosed Anonymously https://priorart.ip.com/IPCOM/000251128, Publication Date: Oct. 17, 2017.

* cited by examiner

COGNITIVE CONTEXTUAL ROUTE NAVIGATION

BACKGROUND

Navigation systems, including those utilized in automobiles and in Internet of Things (IoT) devices, provide users with directions to selected destinations. Many of these navigational systems (and devices) rely on satellite navigation systems to obtain a current position of a device and to correlate data describing the current position to a position on a road. Existing navigational devices, which can be integrated into personal computing devices or can be stand-alone devices, provide many features that enable flexibility in navigation, including destination searches, routing and re-routing, integration with social networks to find contacts, identifying traffic congestion, and identifying points of interest. These devices can receive input from users in a variety of ways, including receiving manual input, voice input, and haptic input. Existing devices can perform dead reckoning, a process of calculating a user's current position by using a previously determined position, or fix, and advancing that position, based upon known or estimated speeds, over elapsed time, and course, by using distance data from sensors attached to a vehicle's drivetrain. A gyroscope and an accelerometer can also be utilized as GPS signal loss and/or multipath can occur during routes that include urban canyons and tunnels. Some existing navigation systems are integrated with weather service providers such that a navigational device can provide enhanced information regarding adverse weather events that may be experienced during a trip, however, this information is not utilized by these existing systems to inform routing functionality.

For many travelers, a best route from a starting point to a destination may not necessarily be the fastest route, but, unfortunately, many existing navigational systems consider "fastest" as synonymous with "best." In addition to reaching a given destination within a minimal amount of time, users utilizing navigational systems for driving, walking, and/or otherwise navigating to a destination, may have personal traits that render a given route better. Additionally, environmental factors that the user could encounter en route could also establish one route as superior to another. One example of an environmental concern that could impact a user experience on a routes (therefore rendering some routes superior to others, for that user) is a prevalence of smog, or other air pollutants. This type of pollution is arguably unhealthy for all users to traverse, but it is particularly problematic for users with various health concerns to navigate routes where they would encounter air pollution.

SUMMARY

Shortcomings of the prior art are overcome and additional advantages are provided through the provision of a method for routing a user based on user-specific considerations. The method includes, for instance: obtaining, by one or more processors, a request to be electronically monitored, from a user, via a computing resource physically proximate to the user, wherein the request comprises authorization to access one or more data sources utilized by the user or proximate to the user, wherein at least one data source of the one or more data sources comprises location data characterizing the physical location of the computing resource; continuously monitoring, by the one or more processors, the authorized one or more data sources to obtain data relevant to the user; generating and training, by the one or more processors, a predictive model, wherein the predictive model is utilized by the one or more processors, to determine a probability that the user will experience a wellness issue based on experiencing one or more environmental factors, based on the continuously monitoring, and obtaining additional data, from one or more computing resources communicatively coupled to the one or more processors, wherein the additional data comprises one or more behaviors indicating the wellness issue and the one or more environmental factors that contribute to the one or more behaviors; obtaining, by the one or more processors, via the computing resource, a request to receive route guidance to a desired destination, via a navigational application executing on the computing resource; and generating, by the one or more processors, a recommended route to the desired destination, based on applying the predictive model to environmental data obtained from a portion of the one or more data sources, wherein the environmental data indicates a given environmental factor present at one or more locations en route to the desired destination, and wherein the predictive model indicates a threshold probability of a wellness issue based on the given environmental factor, and wherein the recommended route avoids the one or more locations.

Shortcomings of the prior art are overcome and additional advantages are provided through the provision of a computer program product for routing a user based on user-specific considerations. The computer program product comprises a storage medium readable by a processing circuit and storing instructions for execution by the processing circuit for performing a method. The method includes, for instance: obtaining, by one or more processors, a request to be electronically monitored, from a user, via a computing resource physically proximate to the user, wherein the request comprises authorization to access one or more data sources utilized by the user or proximate to the user, wherein at least one data source of the one or more data sources comprises location data characterizing the physical location of the computing resource; continuously monitoring, by the one or more processors, the authorized one or more data sources to obtain data relevant to the user; generating and training, by the one or more processors, a predictive model, wherein the predictive model is utilized by the one or more processors, to determine a probability that the user will experience a wellness issue based on experiencing one or more environmental factors, based on the continuously monitoring, and obtaining additional data, from one or more computing resources communicatively coupled to the one or more processors, wherein the additional data comprises one or more behaviors indicating the wellness issue and the one or more environmental factors that contribute to the one or more behaviors; obtaining, by the one or more processors, via the computing resource, a request to receive route guidance to a desired destination, via a navigational application executing on the computing resource; and generating, by the one or more processors, a recommended route to the desired destination, based on applying the predictive model to environmental data obtained from a portion of the one or more data sources, wherein the environmental data indicates a given environmental factor present at one or more locations en route to the desired destination, and wherein the predictive model indicates a threshold probability of a wellness issue based on the given environmental factor, and wherein the recommended route avoids the one or more locations.

Methods and systems relating to one or more aspects are also described and claimed herein. Further, services relating to one or more aspects are also described and may be claimed herein.

Additional features are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
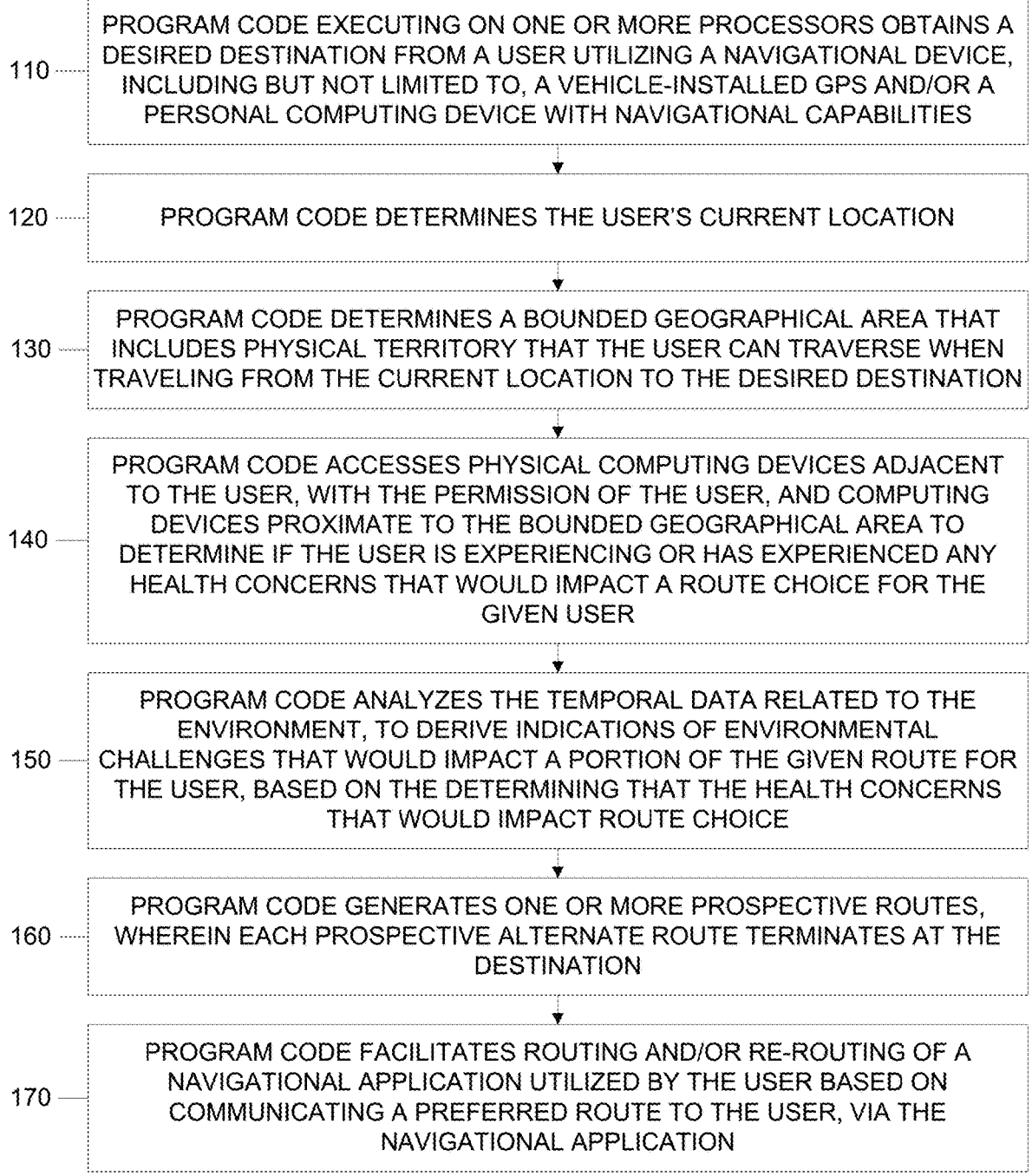
FIG. 1 is a workflow illustrating certain aspects of an embodiment of the present invention.

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Figure 7:
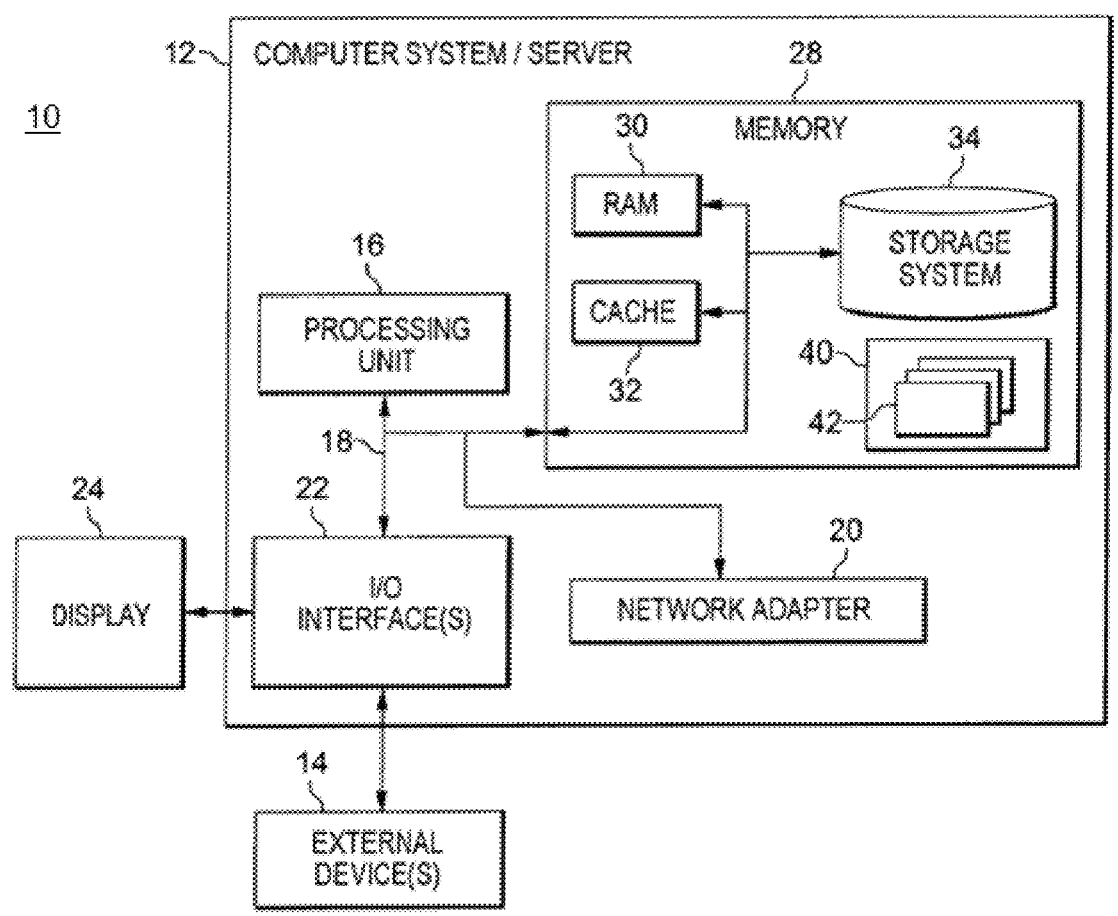
FIG. 7 depicts one embodiment of a computing node that can be utilized in a cloud computing environment.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code, also referred to as one or more programs, is depicted in FIG. 7 as program/utility 40, having a set (at least one) of program modules 42, can be stored in memory 28.

Embodiments of the present invention include a computer-implemented method, a computer program product, and a computer system that include program code executed on at least one processing circuit that provides a customized routing of a user, including suggesting personalized environmentally aware routes to a user, based on identifying user-specific impediments of potential routes and providing the user with a personalized route. To this end, in embodiments of the present invention, program code executing on one or more processors accesses data that is publicly available, as well as personal data, accessed with explicit prior user permission, to determine the personalized route. Specifically, embodiments of the present invention comprise a cognitive smog detector and health-based dynamic router, meaning that the program code can continuously route a given individual based on various personal and environmental conditions, including the health of the individual and of the environment, to allow an individual to reach a destination in a healthful manner. In embodiments of the present invention, the program code can also provide intermittent route updates, based on personalized and environmental considerations. Embodiments of the present invention determine and adjust routes provided progressively and at once, in accordance with personal and environmental factors that include, but are not limited to, smog levels, pollutant levels, personal health characteristics and/or personal medical history considerations of the user (obtained with the express permission of the user), speed of movement of the user, travel speed, desired arrival time, user calendar data (obtained with the express permission of the user), and/or natural language suggestions by the user and others within the perception of various data collection devices. In some embodiments of the present invention, rather than suggest a route to a user, the program code will automatically re-route the user, using a navigational computer application executing on a client device utilized by the user.

In some embodiments of the present invention, the program code provides the following functionality when suggesting or configuring a new route for a user engaged in utilizing routing software to reach a given destination: 1) analyzing devices within a bounded geographic area that provide, with user permission, data describing activity and motion of the user (e.g., motion sensors, including but not limited to a gyroscope and an accelerometer) to identify physical activity patterns of the user; 2) determining environmental factors could impact feasibility of a planned (current) route, by analyzing image capture devices and air quality devices within a vicinity of a user and a user's planned route to obtain environmental data, including but not limited, smog conditions, air pollutants, lighting conditions, fog conditions, local flooding, wind direction, and wind speed etc.; and 3) customizing the new route to the user, based on determining that data obtained based on obtaining permission from the user to access personal devices, including Internet of Things (IoT) devices, associated with the user and/or the routing by the client device, impacts the feasibility of a planned route or indicates a better (new route) than the planned route; this can data include, but is not limited to, user profile attributes, driving patterns, environmental data (including pollution information), health conditions of the user (obtained with the permission of the user), and/or crowd-sourced route information.

Aspects of various embodiments of the present invention are inextricably linked to computing and provide improvements over existing computerized navigational techniques and systems. First, providing computer-assisted route guidance utilizing a navigational device, which may provide computerized route guidance based on communications with one or more of global positioning system (GPS) satellites and/or cellular phone network towers, is inextricably linked to computing, both because of the hardware and the software utilized to enable this functionality. Location services, in general, which include providing route guidance, with a navigational device, which is a computing device, is a functionality that is unique to computing and therefore, inextricably linked to computing. Furthermore, some embodiments of the present invention rely upon implementation within an infrastructure provided by computing devices as program code in embodiments of the present invention utilizes communications capabilities of a 5G communications network and smart channel monitoring tools with existing 4G and compatible platforms to collect and analyze data from various IoT enabled devices placed across in-scope boundary areas as well as IoT enabled sensors and other data servers like media channels and private data operators.

Second, embodiments of the present invention represent an improvement over existing computerized navigational techniques at least because aspects in embodiments of the present invention address identifying spatio-temporal issues (i.e., issues belonging to both space and time or to space-time) that are visually detectable environmental problems at a lower processing cost, which is important in mobile computing, especially when a utilized mobile computing device is maintaining connectivity to additional computing resources, while in motion, in order to provide data for continued navigation support. This low processing/resource cost approach includes program code executed on at least one processor selectively capturing environmental data available from identified (and permissioned) sources, in order to provide a healthful and accurate personalized route to the given user.

From a user-standpoint, embodiments of the present invention provide various advantages over existing navigational systems. As will be illustrated herein, in embodiments of the present invention, the program code optimizes existing smart route selection mechanisms to provide a health-based system for selection of routes for polluted areas, while personalizing the health-based selection to the user based on factors including, but not limited to pattern, nature, and personal characteristics of the user and, optionally a relevant set of individuals. Additionally, the program code provides optimal routes to destinations in case of hazardous environmental conditions, including but not limited to, smog and other environmental conditions to which a user may be sensitive to (e.g., a user with asthma may seek to avoid certain pollutants en route to a destination). Also, embodiments of the present invention utilize temporal conditions, including but not limited to, time, situation, location, and other environmental and user-specific parameters, to determine and manage a route traversed by a user to a desired destination.

Aspects of some embodiments of the present invention provide route guidance to a user (i.e., driver) through a navigational device, including a personal computing device with navigational capabilities, that is efficient, from a processing perspective, and personalized, based on environmental factors, as anticipated to be experienced by the driver. FIG. 1 provides a general workflow 100 of aspects of some embodiments of the present invention. Subsequent figures will expand upon the functionality illustrated in FIG. 1. In some embodiments of the present invention, program code executing on one or more processors obtains a desired destination from a user utilizing a navigational device, including but not limited to, a vehicle-installed GPS and/or a personal computing device with navigational capabilities (110). Based on obtaining the desired destination, the program code determines the user's current location (120). The program code can make this determination based on utilizing location services within the device utilized by the user to request the route assistance (e.g., enter the desire destination) and/or via another computing device proximate to the user which the user has registered with the program code or otherwise provided explicit permission to the program code to access. In some embodiments of the present invention, the program code can utilize a cellular phone of the user to triangulate the position of the user.

In some embodiments of the present invention, based on obtaining the desired destination and the current location of the user, the program code determines a bounded geographical area that includes physical territory that the user can traverse when traveling from the current location to the desired destination (130). The program code determines the bounded area because environmental factors within certain locations in this area can influence whether a given route is an ideal route for a user, or not. For example, certain health considerations, including but not limited to, heavy air pollution, at certain locations, can cause the program code to eliminate any potential route through those areas, or classify those routes as less ideal, for the user. In some embodiments of the present invention, the boundary is dynamic and the program code continuously updates the boundary after a user initiates travel from the current location to the desired destination. As a user traverses a route, various possibilities for changes to the route can present themselves, thus, the program code continuously recognizes the area in which these travel choices can be experienced. In some embodiments of the present invention, the program code updates the dynamic boundary after a pre-defined static time interval, and/or after a pre-defined interval which the program code calculates based on parameters, including, but not limited to, travel. As will be discussed later, the program code collects data within the bounded geographic area, thus, as the bounded area is updated dynamically, the program code will obtain additional data.

In some embodiments of the present invention, program code accesses physical computing devices adjacent to the user, with the permission of the user, and computing devices proximate to the bounded geographical area (e.g., personal computing device, Internet of Things devices, sensors, personal health trackers, physical activity trackers, smart watches, sensors integrated in the vehicle, computing devices integrated into the vehicle, instruments in the vehicle, etc.), to determine if the user is experiencing or has experienced any health concerns that would impact a route choice for the given user (140). While the physical computing devices adjacent to the user generally provide the program code with data related to a health condition of the user, the computing devices proximate to the bounded geographical area provide the program code with data related to environmental conditions which could exacerbate health conditions (pollutants, smog, etc.).

In embodiments of the present invention, the devices accessed by the program code can include devices from the following categories: sensor technologies instrumented within a pre-defined geographical boundary proximate to the user, computing resources of a vehicle being utilized to navigate, and/or personal computing devices of the user. Thus, the program code makes determinations about the user that will impact the route based both on the user's health as well as on the conditions within the pre-defined geographical boundary proximate to the user, before the user starts traveling toward and destination and/or when the user is en route to the destination. Thus, to determine whether a route is suited to a user, based on the user's health, the program code considers environmental conditions in which portions of the previously determined bounded area the user would traverse, based on the route provided to the user. In some embodiments of the present invention, based on environmental conditions on a recommended route changing (which the program code discovers via IoT devices collecting data proximate to locations along the route), the program code can change a route, in-the-fly.

In embodiments of the present invention, the program code can determine if the user is experiencing or has experienced any health concerns that would impact a route choice for the given user, based on utilizing IoT devices associated with the user to assess a condition of the user and based on data obtained by the program code from various IoT devices within a physical area potentially traversed by the user to travel from the current location to the desired destination (i.e., environmental factors that could aggravate health conditions of the individual). As understood by one of skill in the art, the Internet of Things (IoT) is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object or an area, including but not limited to, temperature and humidity. The smart sensors can be utilized to measure temperature, humidity, vibrations, motion, light, pressure and/or altitude. IoT devices also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. Because the smart sensors in IoT devices carry unique identifiers, a computing system that communicates with a given sensor can identify the source of the information. Within the IoT, various devices can communicate with each other and can access data from sources available over various communication networks, including the Internet. Certain IoT devices can also be placed at various locations and can provide data based in monitoring environmental factors at the locations.

The program code analyzes the temporal data related to the environment, to derive indications of environmental challenges that would impact a portion of the given route for the user, based on the determining that the health concerns that would impact route choice (150). Based on determining the presence of an environmental challenge for the user, the program code generates one or more prospective routes, wherein each prospective alternate route terminates at the destination (160). In some embodiments of the present invention, program code interfaces with off-the-shelf navigational software. For example, the program code, based on determining that an environmental challenge exists, can request re-routing from the navigational application executing on the client. Responsive to the request from the program code, the navigational application provides the alternate routes.

In some embodiments of the present invention, rather than utilize personal data related to the user (or in additional to utilizing personal data of the user), the program code can utilize data of individuals that are demographically similar to the user in determining the health condition of a user. A user can elect not grant limited access to personal data to the program code. In this situation, the program code can supplement the unknown by identifying similar individuals, based on the demographic information made available by the user. In accessing permissioned data of similar individuals, the program code will not reveal any personally identifiable information to the user, but, rather, utilize aggregate values to predict likely health concerns/conditions of the user.

In some embodiments of the present invention, as part of determining if the user is experiencing or has experienced any health concerns that would impact a route choice for the given user (140), the program code obtains environmental data relevant to each possible route from the current position to the desired destination and user-specific environmental preference data (e.g., based on user health condition) from the computing devices adjacent to a user and data sources external to a vehicle in which a user is traveling. Based on the connectivity of the client and to both computing devices adjacent to the user (e.g., personal computing device, Internet of Things devices, sensors, personal health trackers, physical activity trackers, smart watches, sensors integrated in the vehicle, instruments in the vehicle, etc.), as well as additional computing resources comprising data sources external to the vehicle (e.g., social media platforms), program code in embodiments of the present invention can access these additional computing resources to gather, with the permission of the user, personal information about the user, as well as data relevant to any potential routes the navigational application may route or re-route a user through, in the bounded geographical area. For example, social media platforms can provide data relevant to a user's environmental preferences, as well as first-hand accounts of weather affected areas en route to the destination. In embodiments of the present invention where the program code retains spatio-temporal data related to environmental conditions discovered by analyzing data captured by IoT devices, the program code can access the repository and obtain data provided by other drivers regarding spatio-temporal conditions at other locations, including locations that the driver would pass through, based on the recommended route provided to the user by the program code.

The program code can utilize this information to generate or update user-specific preference environmental data, which is based on ongoing health monitoring of the user. For example, the user can utilize a personal computing device to connect to various computing resources (e.g., IoT devices and social media platforms) to manage user profiles, configure social media accounts, define preferences, obtain biometrics and other health measurements, etc. The program code in embodiments of the present invention, with the permission of the user, can intercept or observe these communications and/or can take advantage of the connectivity of the personal computing device to these external resources. Based on this connectivity, the program code can obtain data user-specific preference data for user profile, which the program code can store and maintain (e.g., update, based on temporal variations in personal data) on a client associated with the user. In some embodiments of the present invention, the program code can also obtain user-specific preference data by accessing historical travel patterns stored by a device utilized by the user to navigate, when the user is facing specific environmental issues. The user-specific environmental preference data includes personalized environmental risk sensitivities, some of which would be dictated by the health condition of the user, which would provide reasoning behind taking one route over another. Different users may have different priorities towards various environmental problems. The particular sensitivities of a given user can be captured by the program code in that user's user-specific environmental preference data. Thus, the program code personalizes routing to the individual sensitivities of a user, including the specific health-related sensitivities.

In some embodiments of the present invention, the program code facilitates routing and/or re-routing of a navigational application utilized by the user based on communicating a preferred route to the user, via the navigational application (170). In some embodiments of the present invention, the program code, through the interface of a client utilized by the user, suggests routing or re-routing to the user. The suggestion can include data (provided visually and/or audibly) supporting the suggestion with one or more recommendations, based on one or more of the environmental data and/or the user-specific (e.g., health-related) environmental preference data. The user can accept or decline the suggestion. An acceptance would trigger re-routing. In some embodiments of the present invention, the program code automatically facilitates the routing without or re-routing without user interaction. In some embodiments of the present invention, the program code provides route guidance and routing through a graphical user interface (GUI) with various alerts to a user, noting possible environmental issues that the user can experience that could potentially impact the health of the user. In some embodiments of the present invention, the program code displays and/or facilitates the display, on a client, in a GUI, of alert levels in conjunction with areas a user will traverse en route to the desired destination. For example, the program code can display areas with warnings and/or directives, which can be accompanied by color indicators, including but not limited to: "Red-with-alert", "Green-with-good-health", and/or "time-to-go-red-too-much-smog." The final of the alerts demonstrates the ability of the program code to update its perception of health conditions, based on receiving data on an ongoing basis, from one or more devices located proximate to an area being evaluated. In some embodiments of the present invention, the user can provide inputs, in real-time, that override the planned route. Based on these manual inputs, the program code can adjust the route recommended/generated.

Figure 2:
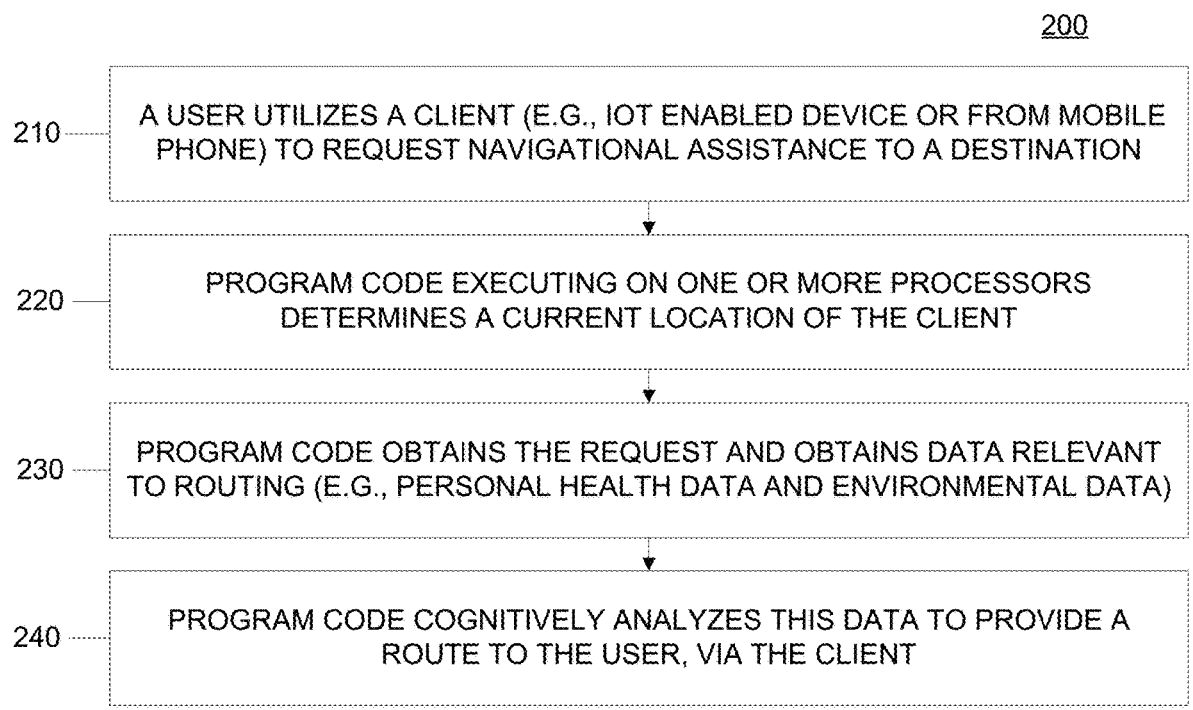
FIG. 2 is a workflow illustrating certain aspects of an embodiment of the present invention.

FIG. 2 is a workflow 200 that illustrates various aspects of some embodiments of the present invention. FIG. 2 is provided to illustrate how in some embodiments of the present invention, program code executing on one or more processors can utilize existing mobile technology infrastructure to route a user to a healthier route, for the user, based on obtaining the user's health-related data (with the permission of the user) and environmental conditions that could impact the health of the user, en route to the destination, in real-time. As understood by one of skill in the art, based on obtaining permission to access personal and health-related data of the user, in advance of routing a user, program code in embodiments of the present invention can provide a route that is more sensitive to the particular user's health concerns. However, should a user withhold permission and should the program code not access personal information, the program code is still able to provide a more "healthy" route, but the routing provided would be based on the environmental factors, without the additional personalization based on the health conditions of the user.

Referring to FIG. 2, in an embodiment of the present invention, a user utilizes a client (e.g., IoT enabled device or from mobile phone) to request navigational assistance to a destination (210). Program code executing on one or more processors determines a current location of the client (220). The program code obtains the request and obtains data relevant to routing (e.g., personal health data and environmental data) (230). The relevant data obtained by the program code to utilize in analyses to determine an optimal route includes, but is not limited to, traffic details, IoT enabled device data, personality insights, data maps, and/or route maps. Program code cognitively analyzes this data to provide a route to the user, via the client (240). The route provided to the user by the program code is an optimal route having minimal health-related obstacles.

Figure 3:
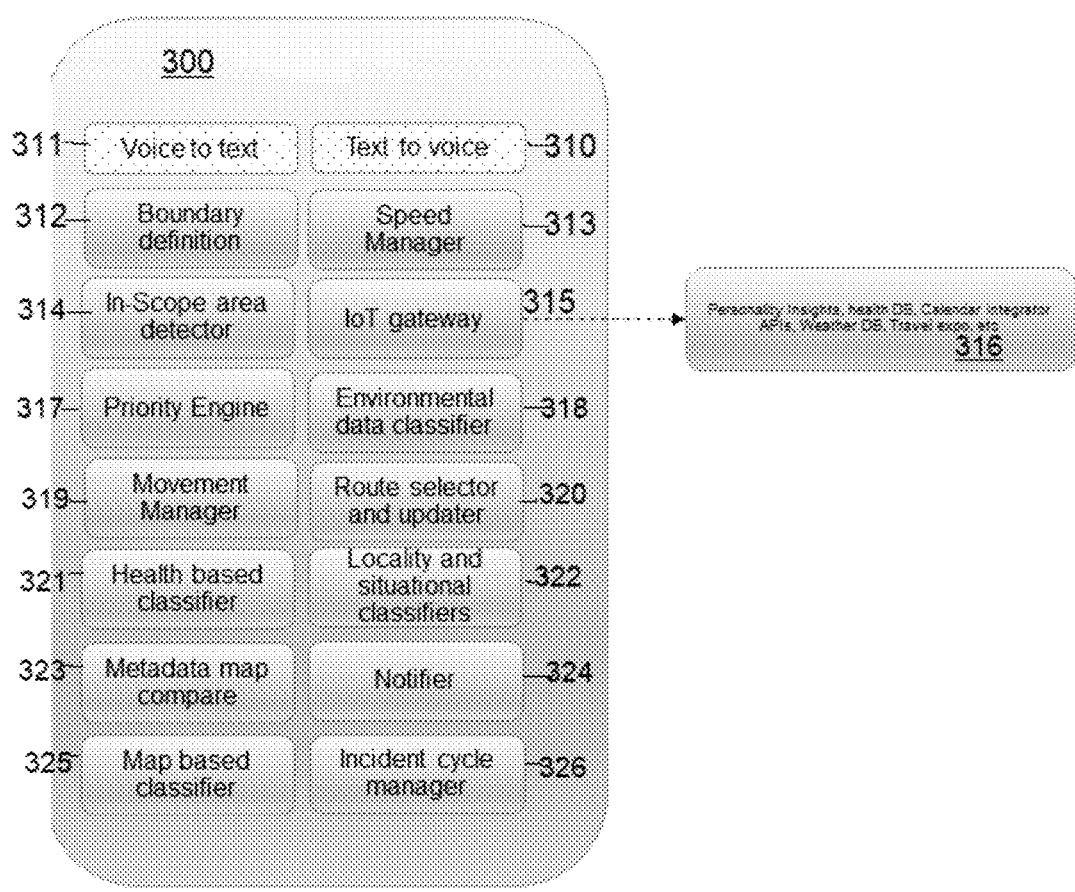
FIG. 3 is an illustration of various aspects of some embodiments of the present invention.

In some embodiments of the present invention, the program code comprises a cognitive engine that analyzes data from various sources to determine an optimal route having minimal health-related obstacles, which performs this cognitive analysis. FIG. 3 is an illustration of aspects of a cognitive engine 300 of some embodiments of the present invention. The program code of the cognitive engine obtains data for analysis and analyzes the data to provide an optimal route. Aspects of the cognitive engine can be implemented locally on a client utilized by a user to request route assistance and/or can be provided to a client, as a service. FIG. 3 provides a non-limiting example of a cognitive engine 300 that can be utilized in embodiments of the present invention. As aforementioned, program code in embodiments of the present invention obtains data related both to the user (with permission) and the environment, from IoT devices located proximate to each. For ease of understanding, various functionalities of the program code are separated into distinct module in FIG. 3. This particular configuration is offered for illustrative purposes only as various functionalities can be grouped across different embodiments of the present invention.

In embodiments of the present invention, program code comprising a cognitive engine 300 obtains and analyzes data in order to recommend an initial route and progressively update the route, as dictated by the analysis of both environmental and personal factors. In some embodiments of the present invention, the cognitive engine obtains the IoT data 316, via an IoT gateway 315. In some embodiments of the present invention, program code comprising an in-scope area detector can locate computing devices, including IoT devices, within the defined bounded area, that can provide environmental information, and computing devices, including IoT devices, proximate to the user and/or registered to the user, which can provide personal (e.g., health-related) information about the user. Before obtaining data from a user, the user provides permission to the program code to communicate with the computing devices and to the data. Permissions may be provided in a granular level such that the user is cognizant of the access he or she enables.

The cognitive engine 300 includes various application programming interfaces (APIs) that allow the program code to obtain and analyze available data and synthesize this data to determine and optimal route. For example, voice to text 311 and text to voice 310 capabilities enable the program code to receive data in various forms and to process it for inclusion in the route generation. As discussed in FIG. 1, the program code defines a boundary for data collection (e.g., FIG. 1, 130). The voice to text 311 and text to voice 310 capabilities comprise a natural language processing (NLP) facility, which can obtain and process non-IoT enabled signals discovered in the bounded area. To define this boundary, the cognitive engine utilizes boundary definition 312, a speed manager 313 (to define intervals for updating the boundary defined), and an in-scope area detector, to recognize IoT devices within the dynamic boundary from which to obtain environmental data. In some embodiments of the present invention, with the permission of the user, some of the data collected via the IoT gateway 315 and/or other communication channels of the cognitive engine 300 includes the user's medical history. As explained herein, the program code can utilize this medical history when generating a route to a desired destination, adjusting the route during the trip, and/or suggesting an alternate route in advance of or during a given trip to the desired destination.

In some embodiments of the present invention, the cognitive engine 300 includes various classifier analysis tools that enable the program code to synthesize contextual data obtained, including health data (obtained with the permission of the user to whom the health data is relevant) and environmental data, and build a framework to utilize in determining an optimal route for a given user from a point or origin and/or an intermittent point, to a desired destination. Classifiers include machine learning algorithms that implements classifications. For example, classifiers can include functions, implemented by classification algorithms, which map input data to a category. As aforementioned, the program code obtains data from various sources, including IoT devices, and the classifiers synthesize the data obtained, such that it is applicable to determining an optimal route for a given user. The program code can continuously update the optimal route, based on new data obtained by the program code and analyzed by the cognitive engine 300. For example, in some embodiments of the present invention, the cognitive engine 300 includes program code comprising an environmental data classifier 318, which analyzes environmental data obtained within the dynamically bounded area (e.g., via the IoT gateway 315 and/or via the NLP mechanisms) and determines how these obtained conditions impact various routing possibilities. Similarly, a health based classifier 321 utilizes health-related data, if available, (e.g., obtained with the permission of the user, via the IoT gateway 315 and/or via the NLP mechanisms), to determine how the user's health will impact various route selections. In some embodiments of the present invention, the program code of the health based classifier 321 enables the program code to inferred environmental conditions like smog, pollution, etc., from data collected through the IoT gateway 315. For example, the program code can obtain data that indicates that the user has difficulty breathing (e.g., asthma) and can classify smog as problematic for the user and generate routes that avoid this condition, for the user to traverse. Certain issues can be anticipated to exist in certain localities and in certain situations. Program code in the cognitive engine referred to as locality and situational classifiers 322 can inject intelligence related to these circumstances into route determinations by the program code. For example, based on historical data obtained via the IoT gateway 315, the program code can determine that a given area becomes treacherous to traverse during rain storms. Thus, during a rain storm, the program code of the cognitive engine would avoid including this locality in a recommended route. The cognitive engine 300 can also include a map based classifier 325, which coordinates data obtained with a map, such that this continuously learning map can be updated and utilized when the program code determines a route. In some embodiments of the present invention, program code of a priority engine 317 ranks various factors identified in the various classifiers, to generate a framework for determining an optimal route.

In embodiments of the present invention, not only can the program code recommend an initial optimal route, the program code can also continuously adjust the route, intermittently, after the user have already started traveling. Thus, should conditions change en route, such that the original route is no longer optimal, the program code can dynamically recommend a new route. Elements of the cognitive engine 300 that enable this real-time functionality include: 1) a movement manager 319 and a speed manager 313, which monitor motion of the user (e.g., through one or more IoT devices associated with the user, registered by the user for monitoring by the program code), 2) a route selector and update 320 mechanism, which obtains data from one or more of the various classifiers and the NLP processing, and selects and updates the route, based on the health data and environmental data, 3) a metadata map compare 323 aspect, which compares map metadata to environmental data to provide additional intelligence regarding a route (initial or route change) being considered for proposal by the program code, and 4) a notifier 324, which communicates an initial route and any changes, in real-time, to a client utilized by the user.

In some embodiments of the present invention, the navigational mechanisms of the cognitive engine 300 are managed by an incident cycle manager 326, which machine learns from users as they traverse the recommended optimal routes. Should a user experience issues (e.g., health issues) on a route, the program code gathers this information and updates the cognitive engine 300, including the metadata map compare 323 aspect, such that the recommendations are improved in the future. Program code in an embodiment of the present invention can obtain data from these personal devices indicating that the user is experiencing an issue (e.g., elevated heartrate, erratic movement, elevated body temperature, etc.). For example, a personal device worn by the user can include an accelerometer and/or a gyroscope. The program code can utilize these motion sensing devices to identify departures from expected behavioral patterns, indicating a health issue. In some embodiments of the present invention, the program code of the movement manager 319 and/or the speed manager 313 monitors movement of a user (e.g., via location services on a client device) and can update data collection frequency, based on movement and/or speed. Basing data collection frequency of movement and/or the speed allows for efficient processing and data handling as data is collected by the program code, based on the movement manager 319, at intervals necessary to evaluate for re-routing and not more often. Program code that performs monitoring (e.g., the movement manager 319 and/or the speed manager 313) can also detect intermediate stops, travel speed and nature and program code of the route selector and updater 320 can consider these factors when dynamically updating path selection.

Figure 4:
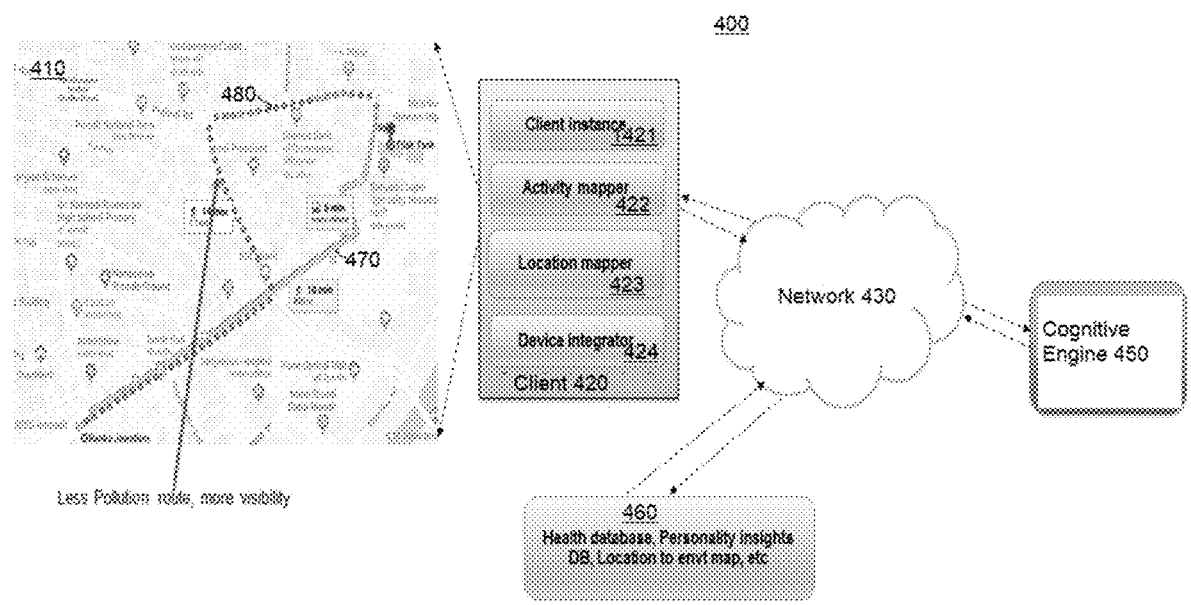
FIG. 4 is an illustration of various aspects of some embodiments of the present invention as implemented within an exemplary technical architecture.

FIG. 4 illustrates a technical architecture 400 into which various aspects of some embodiments of the present invention can be integrated. A user utilizes various navigational and location services (applications) a client 420 computing device, which can be an IoT device. The client instance 421 is an instance of a navigational application executing on the client 420, which displays suggested navigational paths to the user, via a GUI 410. The instance 421 can be one of a proprietary navigational program or a third party program with which the program code of some embodiments of the present invention can communicate to facilitate enhanced functionality. The client 420 includes both an activity mapper 422 and a location mapper 423, which monitor the activities and location of the client 420, and, therefore, the user. Program code of the present invention accessed the location and activity information of the user, as monitored by the client 420, with the express permission of the user, who registers or otherwise authorizes data collection from the client 420 by the program code. Additionally, the user has enabled these services in the client 420 in order for the program code to obtain the data. Program code of embodiments of the present invention, and specifically, of the cognitive engine 450 (e.g., FIG. 3, 300) integrates with the client instance 421 through the device integrator 424. The program code (executing on one or more processors) of the cognitive engine 450 communicates with the client 420, via a network 430, which, in some embodiments of the present invention, is a 5G telecommunications network. In addition to the data obtained by the program code of the cognitive engine 450 from the client 420, the program code can also obtain data to integrate into the cognitive analysis from additional computing devices 460 that the program code of the cognitive engine 450 can access via the network. These additional computing devices can provide data including, but not limited to, health data (e.g., specific to the user, with permission, and general pollution health data, to inform route guidance), personality insights (e.g., specific to the user based on accessing a user's digital wardrobe and monitoring devices utilized by the user and user profiles established by the user, including on social media, with the permission of the user), and/or location-specific environmental data (e.g., data gathered from devices, including IoT devices, proximate to an area that a user will traverse, depending on navigation provided, that indicates environmental conditions in the area).

As illustrated in the GUI 410, the program code of the cognitive engine 450, in embodiments of the present invention, utilizes personal and environmental data to facilitate route guidance that provides a path from a current location to a desired destination (indicated through the client 420), that minimizes negative health impacts of the trip. The GUI 410 is a non-limiting example of a possible display, but as illustrated in FIG. 4, a shortest route 470 (a default of a navigational software) has been re-routed by the program code to provide an optimal route 480 to the user, which is optimal based on the program code of the cognitive engine 450 determining that the optimal route 480 has a decreased likelihood of pollution and a greater possibility of visibility, than the default route 470.

Figure 5:
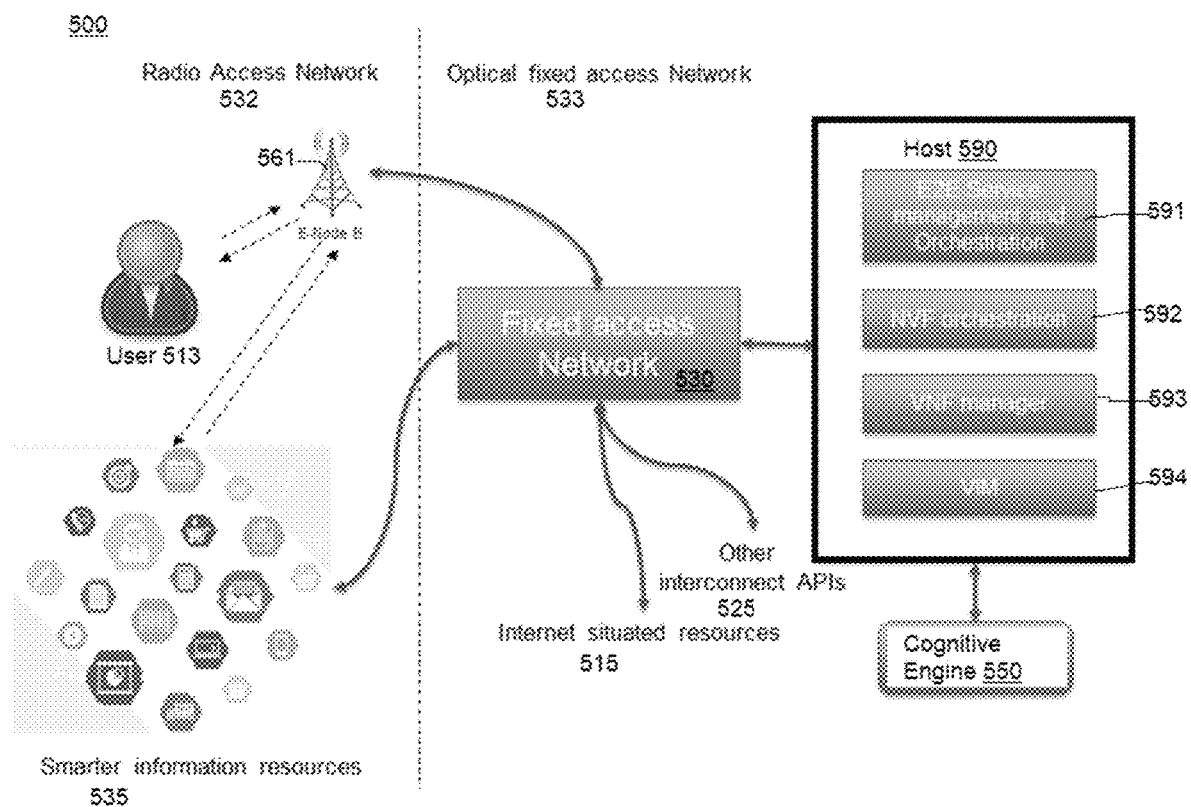
FIG. 5 is an illustration of various aspects of some embodiments of the present invention as implemented within an exemplary technical architecture.

FIG. 5 illustrates a non-limiting example of an implementation 500 of aspects of some embodiments of the present invention as a service. Various aspects of the present invention in this implementation 500 are executed on a host 590, which can be comprised of one or more servers, including servers in a shared computing resources network, such as a cloud. The host 590 manages communications between the cognitive engine 550 and certain other resources, which allows the cognitive engine 550 to gather data utilized in determining an optimal route for a user 513. The host 590 executes exchange to exchange (E2E) service management and orchestration 59, which allows intercommunication between web resources. Meanwhile, the network virtualization function orchestration 592, which enables the host 590 to generate and manage virtual child resources, the virtual network function manager 593, and the virtual machine 594, provide an avenue for communication between the user 513 and the cognitive engine 550. The user 513 can access various aspects of the present invention by communicating with the virtual machine 594, via a client (e.g., a smarter information resource 535).

As discussed above, aspects of some embodiments of the present invention can utilize various communication networks and protocols to facilitate communications from a user 513 to a cognitive engine 550, where the program code of the cognitive engine 550 also utilizes various protocols to obtain data (e.g., from Internet situated resources 515, other APIs 525, and permissioned smarter information resources 535) utilized in an analysis where the results (e.g., a route and/or a change to a route) are ultimately provided to the user 513, via a client GUI (e.g., a smarter information resource 535). Thus, the communication channels illustrated in FIG. 5 include a radio access network 532, with an eNodeB 561 as an endpoint, an optical fixed access network 533, and a fixed access network 530.

Returning to FIG. 1, in some embodiments of the present invention, the program code determines if the user is experiencing or has experienced any health concerns that would impact a route choice for the given user (140). As discussed in FIG. 3, the cognitive engine 300 includes various classifier analysis tools that enable the program code to synthesize contextual data obtained, including health data (obtained with the permission of the user to whom the health data is relevant) and environmental data, to build a framework to utilize in determining an optimal route for a given user from a point or origin and/or an intermittent point, to a desired destination. To generate this framework, in some embodiments of the present invention, the program code applies machine learning algorithms to model the user's health to generate a user health profile. The program code can train these algorithms (e.g., environmental data classifier 318, health based classifier 321, map based classifier 325, and/or priority engine 317) based past and currently observed (via IoT devices) health or wellness patterns for the user (or across all users).

Figure 6:
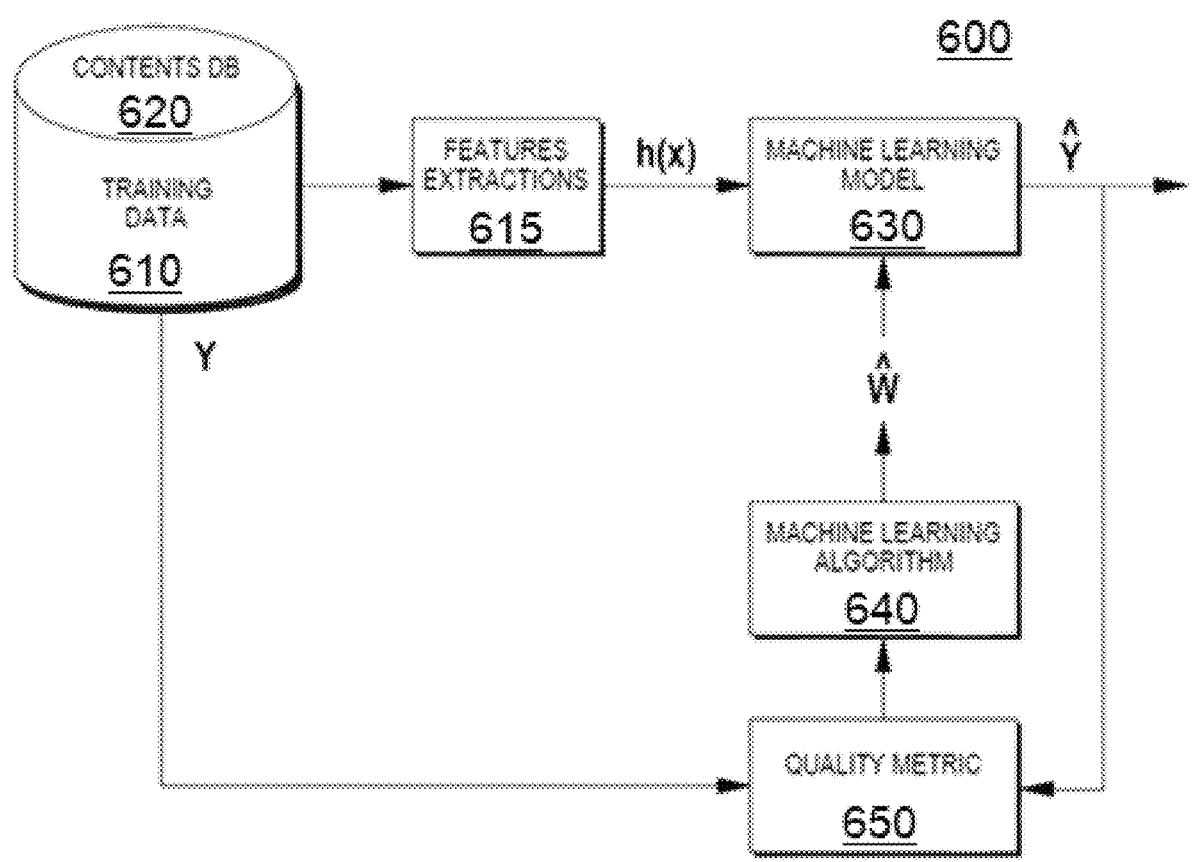
FIG. 6 is an illustration of various aspects of some embodiments of the present invention.

FIG. 6 is an example of a machine learning training system 600 that can be utilized to perform cognitive analyses of sensor (e.g., IoT device) and externally located (social media, etc.) data to generate a user health profile in embodiments of the present invention. Machine learning (ML) solves problems that cannot be solved by numerical means alone. In this ML-based example, program code extracts various features/attributes from training data 640, which may be resident in one or more databases 620 comprising sensor data. The features are utilized to develop a predictor function, h(x), also referred to as a hypothesis, which the program code utilizes as a machine learning model 630. In identifying various features/attributes (e.g., patterns) in the training data 610, the program code may utilize various techniques including, but not limited to, mutual information, which is an example of a method that can be utilized to identify features in an embodiment of the present invention. Further embodiments of the present invention utilize varying techniques to select features (elements, patterns, attributes, etc.), including but not limited to, diffusion mapping, principal component analysis, recursive feature elimination (a brute force approach to selecting features), and/or a Random Forest, to select the features. The program code may utilize a machine learning algorithm 640 to train the machine learning model 630 (e.g., the algorithms utilized by the program code), including providing weights for the conclusions, so that the program code can prioritize various environmental conditions based on severity of the effect of the conditions of the user's health in accordance with the predictor functions that comprise the machine learning model 630. The conclusions may be evaluated by a quality metric 650. By selecting a diverse set of training data 610, the program code trains the machine learning model 630 to identify and weight various attributes (e.g., features, patterns) that correlate to various environmental conditions (e.g., establishing logic for the program code of the priority engine 317).

Referring now to FIG. 7, a schematic of an example of a computing node, which can be a cloud computing node 10. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove. In an embodiment of the present invention, in FIG. 4, the cognitive engine 450, and the additional computing devices 460, and in FIG. 5, the cognitive engine 550 and the host 590 can each be understood as one or more cloud computing nodes 10 (FIG. 7) and if not a cloud computing node 10, then one or more general computing nodes that include aspects of the cloud computing node 10.

In cloud computing node 10 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 7, computer system/server 12 that can be utilized as cloud computing node 10 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed. As understood by one of skill in the art, another area in which aspects of the present invention can be utilized is quantum computing. For example, aspects of embodiments of the present invention can be utilized in conjunction with solving the so-called "dinner party problem" (i.e., "How many people must you have at dinner to ensure that there are a subset of 3 people who all either mutual acquaintances, or mutual strangers?"). Because aspects of the present invention generate correlations between IT issues and business events, utilizing sources both internal and external to a given computing system, program code in embodiments of the present invention is applicable to correlation building to solve other problems. As embodiments of the present invention can be used as an alternative/improved solution to the correlation between business and IT environments for large IT environments with complex businesses processes, applying this functionality to the "dinner party problem" and other situations where correlation building is desired would be advantageous.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
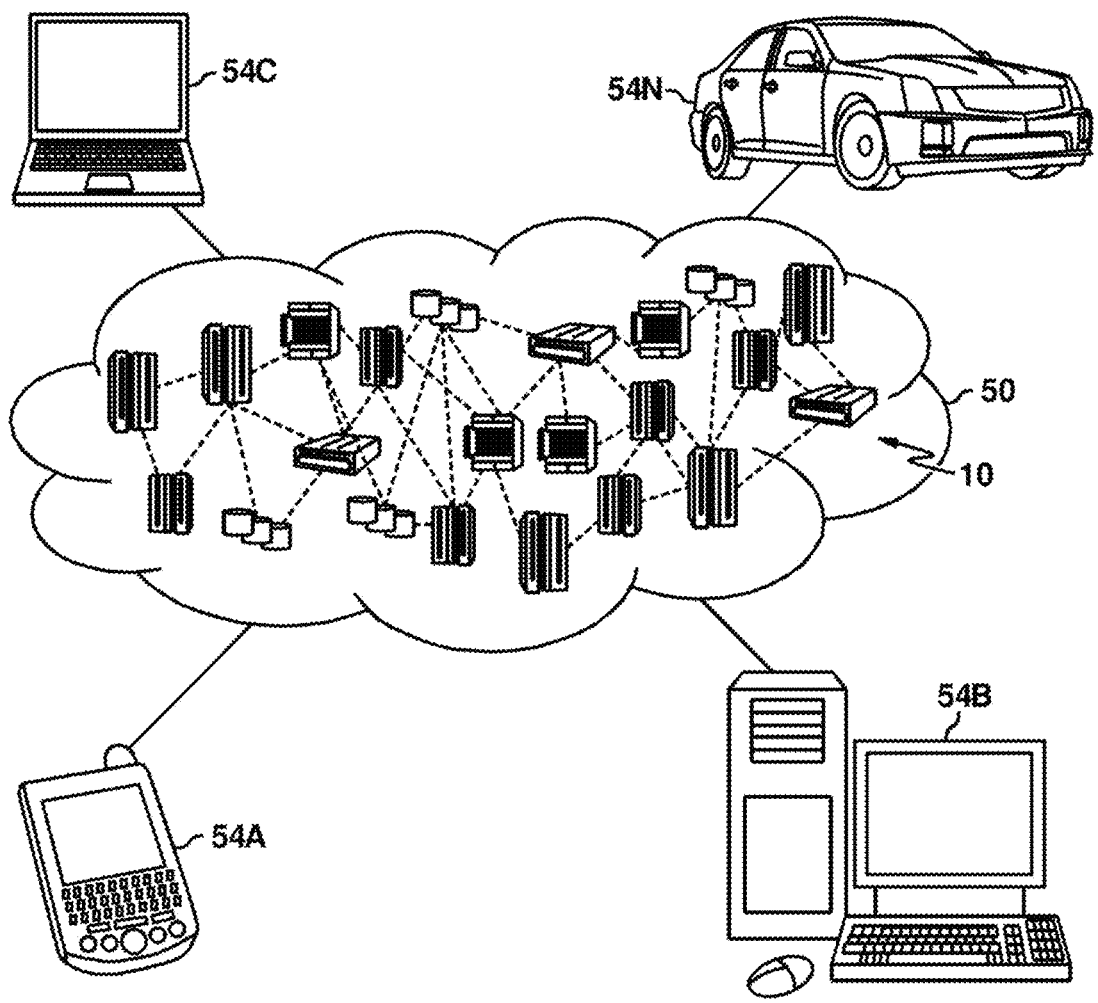
FIG. 8 depicts a cloud computing environment according to an embodiment of the present invention.

Referring now to FIG. 8, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Figure 9:
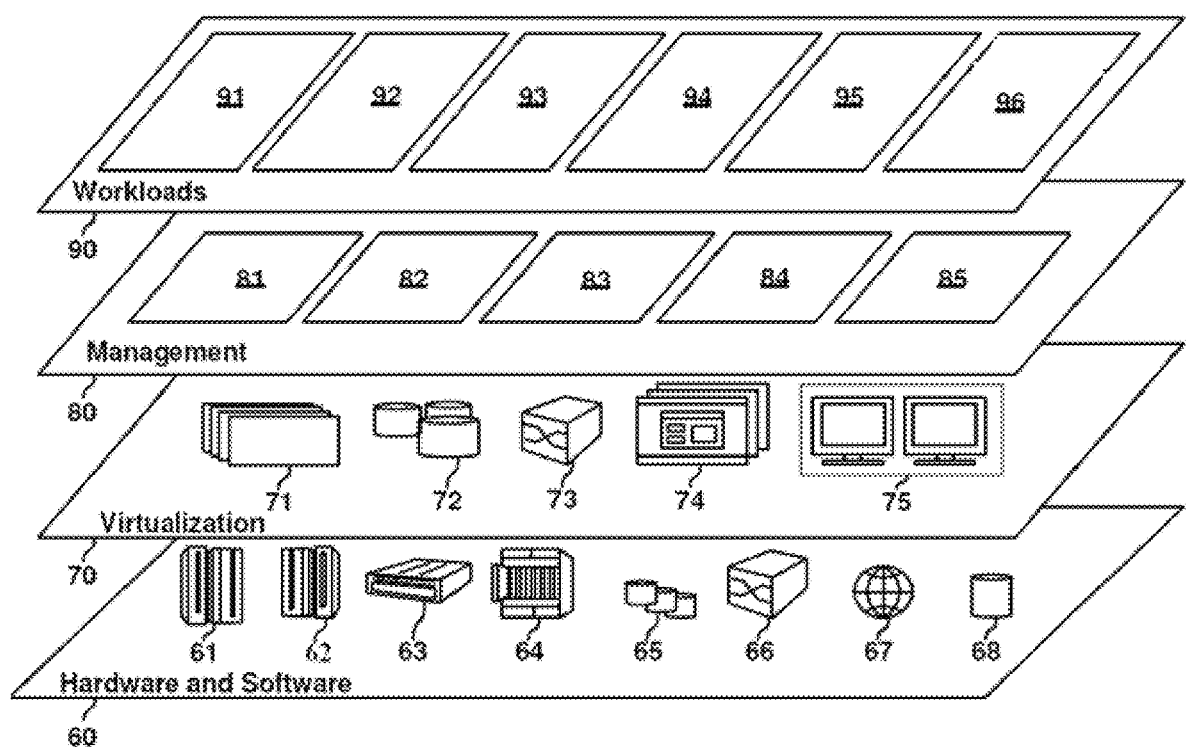
FIG. 9 depicts abstraction model layers according to an embodiment of the present invention.

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and routing a navigational system based on environmental and personalized health considerations 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method, comprising:
    obtaining, by one or more processors, a request to be electronically monitored, from a user, via a computing resource physically proximate to the user, wherein the request comprises authorization to access one or more data sources utilized by the user or proximate to the user, wherein at least one data source of the one or more data sources comprises location data characterizing the physical location of the computing resource;
    continuously monitoring, by the one or more processors, the authorized one or more data sources to obtain data relevant to the user;
    generating and training, by the one or more processors, a predictive model, wherein the predictive model is utilized by the one or more processors, to determine a probability that the user will experience a wellness issue based on experiencing one or more environmental factors, based on the continuously monitoring, and obtaining additional data, from one or more computing resources communicatively coupled to the one or more processors, wherein the additional data comprises one or more behaviors indicating the wellness issue and the one or more environmental factors that contribute to the one or more behaviors;
    obtaining, by the one or more processors, via the computing resource, a request to receive route guidance to a desired destination, via a navigational application executing on the computing resource; and
    generating, by the one or more processors, a recommended route to the desired destination, based on applying the predictive model to environmental data obtained from a portion of the one or more data sources, wherein the environmental data indicates a given environmental factor present at one or more locations en route to the desired destination, and wherein the predictive model indicates a threshold probability of a wellness issue based on the given environmental factor, and wherein the recommended route avoids the one or more locations.

2. The computer-implemented method of claim 1, wherein the one or more locations en route to the desired destination are located within a virtually bounded area, and wherein generating the recommended route further comprises:
    determining, by the one or more processors, based on accessing the location data at the from least one data source, a starting point for the route guidance to the desired destination;
    utilizing, by the one or more processors, the desired destination and the starting point to generate the virtually bounded area comprising physical territory traversed on prospective routes from the starting point to the desired destination;
    locating, by the one or more processors, the portion of the one or more data sources comprising one or more computing devices proximate to portions of the virtually bounded area, wherein the one or more computing devices comprise sensors;
    configuring, by the one or more processors, the sensors to monitor the one or more environmental factors within a proximity of each of the sensors; and
    obtaining, by the one or more processors, from the one or more computing devices, via the sensors, environmental data comprising the given environmental factor at the one or more locations.

3. The computer-implemented method of claim 1, where in the given environmental factor is selected from the group consisting of a pollutants and smog.

4. The computer-implemented method of claim 1, further comprising:
    facilitating, by the one or more processors, an action in the navigational application related to providing route guidance to the desired destination, via the recommended route.

5. The computer-implemented method of claim 4, wherein the action is selected from the group consisting of: automatically changing existing route guidance in the navigational application to provide revised route guidance to the user, via the recommended route, through the computing resource, prompting the user, through an interface of the computing resource, to confirm accepting the route guidance to the desired destination, via the recommended route, and automatically providing the route guidance, via the recommended route, to the user.

6. The computer-implemented method of claim 5, wherein the action consists of prompting the user to confirm the changing the route guidance to the revised route guidance, the method further comprising:
 obtaining, by the one or more processors, a response to the prompting;
 updating, by the one or more processors, the predictive model based on the response.

7. The computer-implemented method of claim 5, wherein the action consists of prompting the user to confirm the changing the route guidance to the revised route guidance, wherein the prompting comprises a description of the given environmental condition avoided in the recommended route.

8. The computer-implemented method of claim 1, wherein the recommended route comprises a shortest route to the desired destination avoiding the one or more locations en route to the destination.

9. The computer-implemented method of claim 1, wherein the computing resource and the one or more processors are communicatively coupled via a 5G communications network.

10. The computer-implemented method of claim 2, wherein the configuring further comprises configuring the sensors to monitor the one or more environmental factors at a pre-defined interval.

11. The computer-implemented method of claim 10, wherein at least one data source of the one or more data sources comprises data characterizing motion and speed of the user, and wherein the pre-defined interval is proportional to the motion and speed.

12. The computer-implemented method of claim 11, wherein the virtually bounded area is dynamic and based on the motion and speed.

13. A computer program product comprising:
 a computer readable storage medium readable by one or more processors and storing instructions for execution by the one or more processors for performing a method comprising:
  obtaining, by the one or more processors, a request to be electronically monitored, from a user, via a computing resource physically proximate to the user, wherein the request comprises authorization to access one or more data sources utilized by the user or proximate to the user, wherein at least one data source of the one or more data sources comprises location data characterizing the physical location of the computing resource;
  continuously monitoring, by the one or more processors, the authorized one or more data sources to obtain data relevant to the user;
  generating and training, by the one or more processors, a predictive model, wherein the predictive model is utilized by the one or more processors, to determine a probability that the user will experience a wellness issue based on experiencing one or more environmental factors, based on the continuously monitoring, and obtaining additional data, from one or more computing resources communicatively coupled to the one or more processors, wherein the additional data comprises one or more behaviors indicating the wellness issue and the one or more environmental factors that contribute to the one or more behaviors;
  obtaining, by the one or more processors, via the computing resource, a request to receive route guidance to a desired destination, via a navigational application executing on the computing resource; and
  generating, by the one or more processors, a recommended route to the desired destination, based on applying the predictive model to environmental data obtained from a portion of the one or more data sources, wherein the environmental data indicates a given environmental factor present at one or more locations en route to the desired destination, and wherein the predictive model indicates a threshold probability of a wellness issue based on the given environmental factor, and wherein the recommended route avoids the one or more locations.

14. The computer program product of claim 13, wherein the one or more locations en route to the desired destination are located within a virtually bounded area, and wherein generating the recommended route further comprises:
 determining, by the one or more processors, based on accessing the location data at the from least one data source, a starting point for the route guidance to the desired destination;
 utilizing, by the one or more processors, the desired destination and the starting point to generate the virtually bounded area comprising physical territory traversed on prospective routes from the starting point to the desired destination;
 locating, by the one or more processors, the portion of the one or more data sources comprising one or more computing devices proximate to portions of the virtually bounded area, wherein the one or more computing devices comprise sensors;
 configuring, by the one or more processors, the sensors to monitor the one or more environmental factors within a proximity of each of the sensors; and
 obtaining, by the one or more processors, from the one or more computing devices, via the sensors, environmental data comprising the given environmental factor at the one or more locations.

15. The computer program product of claim 13, where in the given environmental factor is selected from the group consisting of a pollutants and smog.

16. The computer program product of claim 13, further comprising:
 facilitating, by the one or more processors, an action in the navigational application related to providing route guidance to the desired destination, via the recommended route.

17. The computer program product of claim 16, wherein the action is selected from the group consisting of: automatically changing existing route guidance in the navigational application to provide revised route guidance to the user, via the recommended route, through the computing resource, prompting the user, through an interface of the computing resource, to confirm accepting the route guidance to the desired destination, via the recommended route, and automatically providing the route guidance, via the recommended route, to the user.

18. The computer program product of claim 17, wherein the action consists of prompting the user to confirm the changing the route guidance to the revised route guidance, the method further comprising:
- obtaining, by the one or more processors, a response to the prompting;
- updating, by the one or more processors, the predictive model based on the response.

19. A system comprising:
- a memory;
- one or more processors in communication with the memory;
- program instructions executable by the one or more processors via the memory to perform a method, the method comprising:
  - obtaining, by the one or more processors, a request to be electronically monitored, from a user, via a computing resource physically proximate to the user, wherein the request comprises authorization to access one or more data sources utilized by the user or proximate to the user, wherein at least one data source of the one or more data sources comprises location data characterizing the physical location of the computing resource;
  - continuously monitoring, by the one or more processors, the authorized one or more data sources to obtain data relevant to the user;
  - generating and training, by the one or more processors, a predictive model, wherein the predictive model is utilized by the one or more processors, to determine a probability that the user will experience a wellness issue based on experiencing one or more environmental factors, based on the continuously monitoring, and obtaining additional data, from one or more computing resources communicatively coupled to the one or more processors, wherein the additional data comprises one or more behaviors indicating the wellness issue and the one or more environmental factors that contribute to the one or more behaviors;
  - obtaining, by the one or more processors, via the computing resource, a request to receive route guidance to a desired destination, via a navigational application executing on the computing resource; and
  - generating, by the one or more processors, a recommended route to the desired destination, based on applying the predictive model to environmental data obtained from a portion of the one or more data sources, wherein the environmental data indicates a given environmental factor present at one or more locations en route to the desired destination, and wherein the predictive model indicates a threshold probability of a wellness issue based on the given environmental factor, and wherein the recommended route avoids the one or more locations.

20. The system of claim 19, wherein the one or more locations en route to the desired destination are located within a virtually bounded area, and wherein generating the recommended route further comprises:
- determining, by the one or more processors, based on accessing the location data at the from least one data source, a starting point for the route guidance to the desired destination;
- utilizing, by the one or more processors, the desired destination and the starting point to generate the virtually bounded area comprising physical territory traversed on prospective routes from the starting point to the desired destination;
- locating, by the one or more processors, the portion of the one or more data sources comprising one or more computing devices proximate to portions of the virtually bounded area, wherein the one or more computing devices comprise sensors;
- configuring, by the one or more processors, the sensors to monitor the one or more environmental factors within a proximity of each of the sensors; and
- obtaining, by the one or more processors, from the one or more computing devices, via the sensors, environmental data comprising the given environmental factor at the one or more locations.

* * * * *